United States Patent [19]

Fletcher

[11] Patent Number: 5,042,948
[45] Date of Patent: Aug. 27, 1991

[54] INDUSTRIAL COLORIMETER HAVING LAMP AGING COMPENSATION MEANS

[75] Inventor: Thomas A. Fletcher, Freeport, Ill.
[73] Assignee: Honeywell Inc., Minneapolis, Minn.
[21] Appl. No.: 538,363
[22] Filed: Jun. 14, 1990
[51] Int. Cl.[5] ............................................. G01J 3/50
[52] U.S. Cl. ...................................... 356/328; 364/526
[58] Field of Search ............... 356/319, 326, 328, 402, 356/406, 407, 408, 416, 419, 425; 364/526, 498

[56] References Cited
U.S. PATENT DOCUMENTS 4,076,421  2/1978  Kishner ............................... 356/236
4,449,821  5/1984  Lee ...................................... 356/319

Primary Examiner—F. L. Evans
Attorney, Agent, or Firm—Robert B. Leonard

[57] ABSTRACT

A colorimeter provides compensation for changes in the color signature of an object due to lamp aging. A current measuring circuit measures current to the lamp during an initial training of the colorimeter and stores a value $I_T$ indicative of the lamp current at training. When an object is scanned by the colorimeter, lamp current is again sensed and assigned a value $I_S$. Comparison between a sensed color signature and a stored color signature then occurs. Compensation is accomplished by modifying one of the two signatures by a ratio including $I_S$ and $I_T$.

22 Claims, 2 Drawing Sheets

INDUSTRIAL COLORIMETER HAVING LAMP AGING COMPENSATION MEANS

BACKGROUND OF THE INVENTION

This invention is directed towards the field of color signature sensors used in process automation. More specifically, the invention is a method and an apparatus which performs color recognition of objects for the purposes of identification, sorting or matching.

Colorimeters are well known devices used for characterizing the color of an object and comparing the color of an object to the color of other objects. A lamp, either in the colorimeter or an external source, provides illumination which is reflected by or transmitted through the object and transmitted back to a device which disperses light into an array of wavelength components. A detector array then converts the array of wavelength components into discrete signals which are representative of a color signature of the object. The discrete signals are then sent to an analog to digital converter and then on to a processor for processing. Processing involves a component by component subtraction of sensed component values from stored component values to produce a relative signature difference. Generally, as long as the relative signature difference falls within predetermined limits, the color of the sensed object will be acceptable.

A problem associated with colorimeters is that as the illuminating lamp ages, the color and intensity of the light produced by the lamp can change. This, in turn, causes the color signature of a sensed object to vary with the age of the lamp. This variation in color signature may result in many acceptable pieces being discarded due to erroneous color sensing.

One attempted solution to the problem of lamp aging i to increase the lamp voltage as the lamp ages in order to maintain a constant intensity and color output. However, it has been shown that changing the lamp voltage significantly affects lamp life.

$$(life_{actual}/life_{design}) = (V_{design}/V_{actual})^{10 \sim 14}$$

This means that a voltage increase of five percent will result in an approximate reduction in life of fifty percent.

Another possible solution to the problem of lamp aging is frequent recalibration of the colorimeter. However, this is only feasible in a laboratory environment. In commercial environments, access to the colorimeter may be difficult. Further, frequent recalibration increases the costs of scanning.

Thus, it is an object of the present invention to provide colorimetric sensing which compensates for lamp aging without adversely affecting lamp life. It is a further object of the present invention to provide colorimetric sensing which compensates for lamp aging without requiring frequent recalibration.

SUMMARY OF THE INVENTION

The present invention is a method and apparatus for eliminating the effects of lamp aging in colorimetric sensing. The inventive colorimeter comprises a lamp, a current sensor for determining the electrical current used by the lamp, a diffraction grating for separating light into its component wavelengths, a detector array for sensing the component wavelengths and a processor which includes a compensation means. The processor compares sensed component values with stored component values to produce a signature difference or DELTA. The compensation means causes the stored component value to be adjusted by a factor based on a ratio of the sensed lamp current with a stored lamp current. The ratio of sensed lamp current and stored lamp current can be raised to a predetermined exponent for optimum results.

DESCRIPTION OF THE PREFERRED EMBODIMENT

Figure 1:
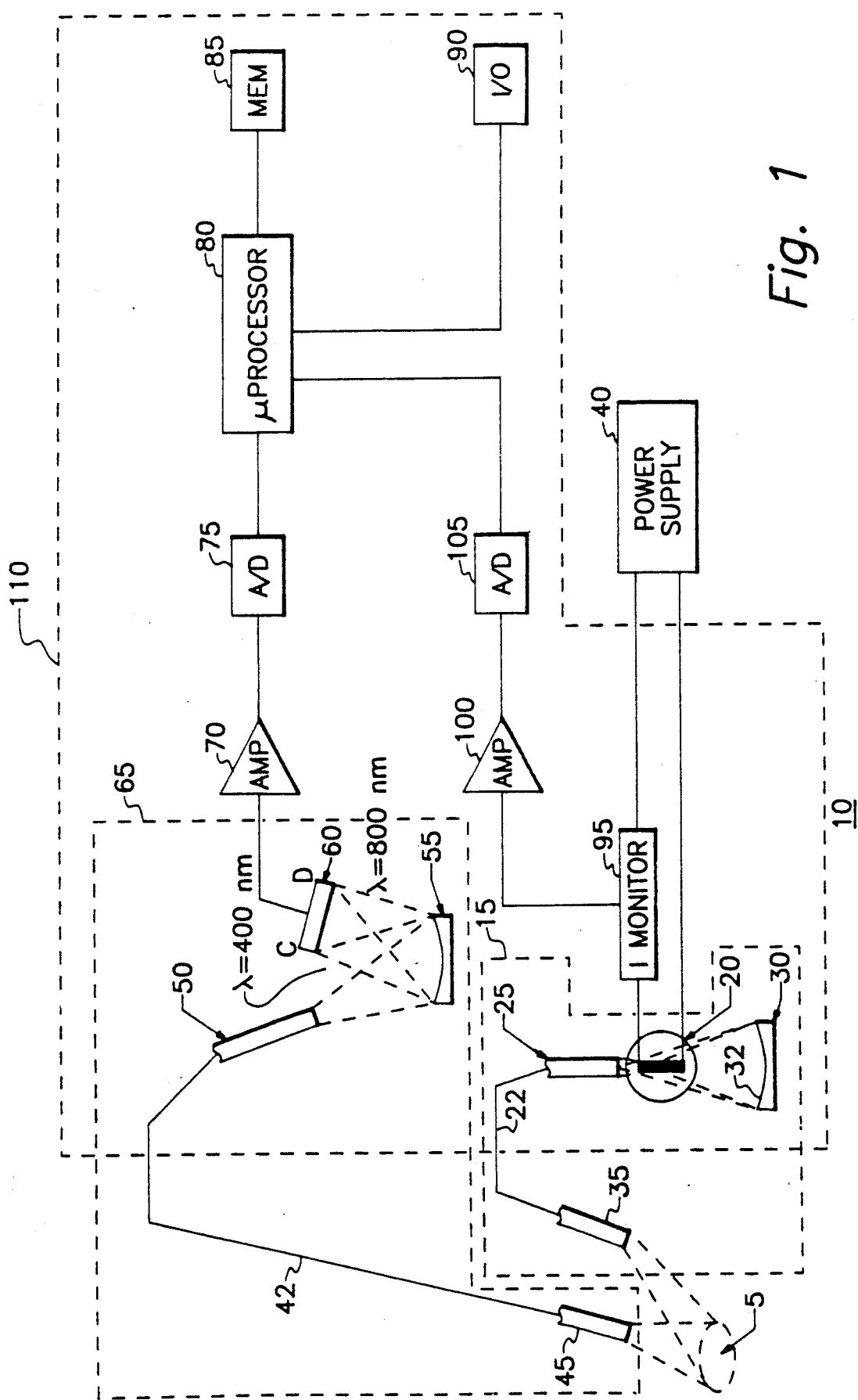
FIG. 1 is a block diagram of the inventive colorimeter and an object to be analyzed.

A preferred embodiment of the inventive colorimeter is shown in FIG. 1. The colorimeter 10 is used to detect the color signature of an object 5.

Lighting means 15 is used to illuminate object 5. In one implementation, lighting means 15 comprises a lamp 20, a mirror 30 and optical fiber 22. Lamp 15 is generally a halogen incandescent lamp. Power supply 40 is connected to lamp 15 to provide electrical power.

First optical fiber 22 is used to transmit light from lamp 20 to object 5. First optical fiber 22 has two ends, a light receiving end 25 positioned near lamp 20 and a light exiting end 35 positioned near a location where objects such as object 5 are to be analyzed.

Mirror 30 is positioned near lamp 20 opposite light receiving end 25. Mirror 30 has a concave side 32 which faces the lamp 20 and focuses light on the light receiving end of optical fiber 22. Use of such a mirror and first optical fiber is optional, but by using the mirror and first optical fiber, an increased light intensity may be transmitted to the object. Collectively, the mirror and the first optical fiber are known are light focusing means.

Object 5 will generally reflect a portion of the light transmitted to it by illumination means 15. Alternatively, object 5 may transmit light therethrough as where the object being measured is a liquid. The amount of and composition of the reflected or transmitted light depends upon the surface and color of the object. The present embodiment could be used equally as well in measuring either reflected or transmitted light, however, the focus in this description will be on reflected light. The reflected light will be carried by a second optical fiber 42 from object 5 to a dispersing element 55. Second optical fiber 42 has two ends, light receiving end 45 positioned near the object and a light exiting end 50. Reflected light leaving light exiting end 50 strikes dispersing element 55. Dispersing element 55 may be a diffraction grating. The reflected light is then broken into its component wavelengths and reflected to detector array 60. For this embodiment, dispersing element 55 disperses and provides a flat field focus of the spectrum (400 nm to 800 nm) on detector array 60. The focused spectrum strikes array detector 60 with 400 nm light at side C and 800 nm light at side D.

The light dispersed and reflected by dispersing element 55 is directed toward a detector array 60. Detector array 60 may be comprised of a linear sequence of N photodetectors. Here, N equals 120. Each photodetector is adapted to produce an electrical signal when light of a predetermined frequency impinges thereon. The magnitude of the signal is directly proportional to the intensity of the light which strikes the photodetectors. A convenient shorthand notation for the second optical fiber, the dispersing element and the detector array is a sensing means 55.

The detector array produces an analog signal indicative of the color signature of object 5. The analog signal is amplified by amplifier 70 and then digitized by A/D converter 75 thus creating a 1XN array of sensed component values. After digitization, the array of sensed values is sent to processor 80 for processing.

Processing of the digital array involves a comparison between each of the components of the array and each component of a stored component array. The stored component array is a base line color signature to which all sensed objects will be compared. The colorimeter is "trained" before it is used by having the sensing means sense, digitize and store color information from a sample object. The sample object must have the surface and color desired of all the objects to be analyzed. The stored component array is stored in memory 85 and is made up of N stored component values. Selection of a mode of operation for the colorimeter can be controlled by input/output controller 90.

Lastly, housing 110 is used to enclose some of the parts of the colorimeter.

Figure 3:
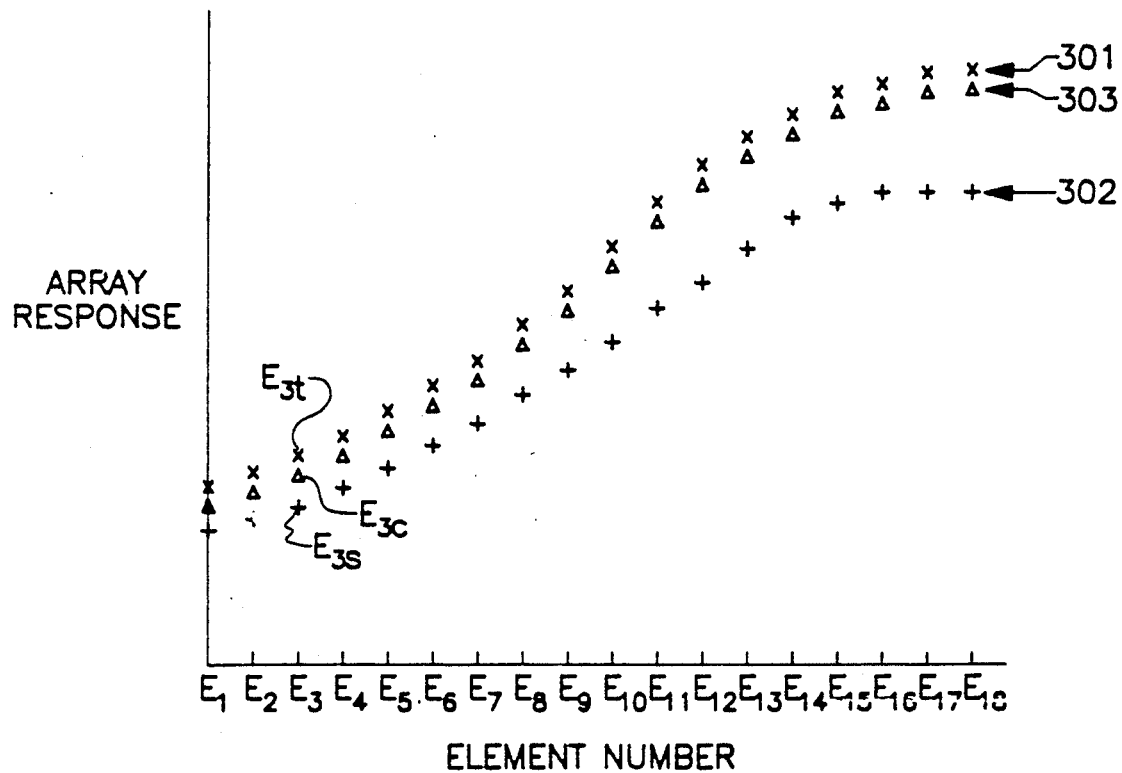
FIG. 3 is comparison between a stored color signature and the sensed color signature with and without compensation.

As was already suggested, each of the components of the sensed wavelength component array is compared with a corresponding component from the stored component array. This can be better understood with reference to FIG. 3. In FIG. 3, curve 301 is representative of the color signature which is stored during the training of the sensor. Curve 302 is the sensed component wavelength array from an object that has been scanned. Looking at one representative component, processor 80 begins by determining the difference between each of the stored component values and the sensed component wavelength values. For example, the processor 80 would subtract the sensed component values $E_{3S}$ from stored component values $E_{3T}$ to produce a DELTA. If the calculated DELTA fell outside predetermined limits, the object which produced this color signature would be deemed to have an unacceptable color and thus would be discarded. However, this DELTA may in part be due to aging of the lamp.

In another scheme, the DELTA for each pair of elements is calculated, then the DELTAS are summed. If the sum of the DELTAS then falls outside predetermined limits, the object is deemed unacceptable.

To account for the problem of aging of the lamp when determining the DELTA, current monitor 95 is placed in the power supply lines for lamp 20. The output of the current supply monitor is sent to amplifier 100 and then on to analog to digital converter 105. The digitized current signal is then passed onto microprocessor 80 and is called the sensed current value. The sensed current value is then used in a ratio with a trained current value to eliminate the effects of lamp aging from a color signature of a scanned object. During the aforementioned training of the sensor, the current used by lamp 20 is also determined and stored in memory 85. For convenience, this trained current will be called $I_T$ or the trained current value.

Through experiment, it has been determined that light intensity is related to lamp current through the equation:

$$(I_C/I_T)^{1.85} = (L_C/L_T)^{0.313}$$

Using the above equation, we can compensate for lamp aging in the calculation of DELTA. There are two ways of doing this. First, the stored component values could be multiplied by $(I_C/I_T)^{5.907}$. Thus the equation for DELTA would be $E_C - E_T(I_C/I_T)^{5.907} =$ DELTA.

The second way to correct for lamp aging mathematically is by multiplying the sensed wavelength component values by $(I_T/I_C)^{5.907}$. Thus, DELTA would be calculated by $E_T - E_C(I_T/I_C)^{5.907} =$ DELTA.

Once DELTA has been calculated, there are at least two ways in which it can be used. First, each DELTA can be reviewed to determine if it falls within predetermined limits. Second, the absolute values of the DELTAS may be summed, and the sum then compared to predetermined limits.

Referring once again to FIG. 3, the effects of using a compensation factor in the calculation of DELTA can be shown. Curve 301 is representative of the stored component values. Curve 302 is representative of the sensed wavelength component values. Curve 303 represents a color signature after compensation has been applied. Note that the compensated curve is closer to the trained curve.

Figure 2:
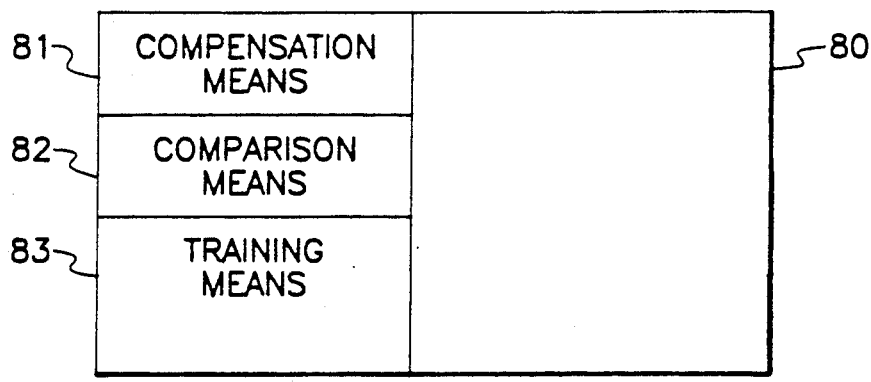
FIG. 2 is a functional diagram of the processor used by the inventive colorimeter.

FIG. 2 shows some parts of processor 80. In FIG. 2, compensation means 81 is used to calculate the correction factor used in the above equations. Comparison means 82 takes the compensation factor, the stored component value and the sensed wavelength component value and produces a DELTA therefrom. Training means 83 is used to create a string of stored component values representative of a color signature. One processor which could be used is an Intel 80C 196 processor.

The foregoing has been a description of a novel and non-obvious colorimeter which provides output compensation for lamp aging. The inventor does not intend to be limited to only the embodiments shown and described in the application. Instead, the scope of the applicant's invention can be determined by the claims appended hereto.

I claim:

1. Apparatus for determining the acceptability of the color of an object, comprising:

Lighting means for illuminating the object with light;

Light sensing means in communication with said lighting means, said light sensing means creating an array of sensed component values representative of the intensity of light received from the object;

Current sensing means for determining an amount of current sued to cause said light and produce a sensed current value indicative of said current; and A processor having compensation means connected to said lighting means, said current sensing means and said light sensing means, said processor generating a difference value which is the difference between each of said sensed component values and a product of corresponding stores values multiplied by an intensity correction factor produced by said compensation means.

2. The apparatus of claim 1, wherein:

said intensity correction factor is equal to said sensed current value divided by a stored current value.

3. The apparatus of claim 2, wherein:

said intensity correction factor is equal to said sensed current value divided by a predetermined current, the quantity being raised to the 5.907th power.

4. The apparatus of claim 3, wherein:
said lighting means comprises a lamp and a light focusing means;
said sensing means comprises a diffraction grating for decomposing reflected light into a predetermined number of components having discrete wavelengths, and an array detector positioned to receive said predetermined number of components and producing a predetermined number of variable electrical signals each of which varies with the intensity of light impinging thereon; and
said current sensing means comprises a current monitor connected to said lamp for producing said sensed current value.

5. The apparatus of claim 4, wherein said light focusing means is comprised of:
an optical fiber for transmitting light from said lamp to the object; and
a mirror for reflecting light received from said lamp onto said optical fiber.

6. The apparatus of claim 5, wherein:
said processor produces an error output if said difference value is outside predetermined limits.

7. The processor of claim 5, wherein:
said processor producing an error output if a sum of said difference values is outside of predetermined limits.

8. Apparatus for determining the acceptability of the color of an object, comprising:
a lighting means for illuminating the object with light;
Light sensing means in communication with said lighting means, said sensing means creating an array of sensed wavelength component values representative of the intensity of light received from the object;
Current sensing means for determining an amount of current used to cause said light and produce a sensed current value indicative of electric current used to generate said lights; and
A processor having compensation means connected to said lighting means, said current sensing means and said light sensing means, said processor generating a difference value which is the difference between each value of an array of stored component values and a product of said wavelength's component value multiplied by an intensity correction factor produced by said compensation means.

9. The apparatus of claim 8, wherein:
said intensity correction factor is equal to a stored current value divided by said sensed current value.

10. The apparatus of claim 9, wherein:
said intensity correction factor is equal to a predetermined current divided by said electric current value, the quantity being raised to the 5.907th power.

11. The apparatus of claim 10, wherein:
said lighting means comprises a lamp and a light focusing means;
said sensing means comprises a diffraction grating for decomposing reflected light into a predetermined number of components having discrete wavelengths, and an array detector positioned to receive said predetermined number of components and producing a predetermined number of variable electrical signals each of which varies with the intensity of light impinging thereon; and
said current sensing means comprises a current monitor connected to said lamp for producing said sensed current value.

12. The apparatus of claim 11, wherein said light focusing means is comprised of:
an optical fiber for transmitting light from said lamp to the object; and
a mirror for reflecting light received from said lamp onto said optical fiber.

13. The apparatus of claim 12, wherein:
said processor produces an error output if said difference value is outside predetermined limits.

14. The processor of claim 13, wherein:
said processor produces an error output if a sum of said difference values is outside of predetermined limits.

15. A method for determining the acceptability of the color of an object, comprising the steps of:
Illuminating the object;
Sensing an amount of electric current required to illuminate the object;
Sensing light received form the object;
Separating the received light into sensed component values;
Dividing the sensed current value by a stored current value to produce a current product;
Raising said current product to a pre-selected power to produce an intensity correction factor; and
Determining a different value between each of said sensed component values and a product of corresponding stored component values and said intensity correction factor.

16. The method of claim 15, comprising the further step of:
generating a first output if all of the difference values are within preselected limits and a second output if any of the difference values is not within a preselected limit.

17. The method of claim 15, comprising the further step of:
generating a first output if the sum of all of the difference values is within preselected limits and a second output if the sum of the difference values is not within a preselected limit.

18. A method for determining the acceptability of the color of an object, comprising the steps of:
Illuminating the object;
Sensing an amount of electric current required to illuminate the object;
Sensing light received from the object;
Separating the received light into sensed component values;
Dividing a stored current value by a sensed current value to produce a current product;
Raising said current product to a pre-selected power to produce an intensity correction factor; and determining a different value between each of an array of stored component values and a product of a corresponding value of said sensed component values and said intensity correction factor.

19. The method of claim 18, comprising the further step of:
generating a first output if all of the difference values are within preselected limits and a second output if any of the difference values is not within a preselected limit.

20. The method of claim 18, comprising the further step of:

generating a first output if the sum of all of the difference values is within preselected limits and a second output if the sum of the difference values is not within a preselected limit.

21. An improved apparatus for determining the acceptability of color of an object of the type including a lighting means to light the object, sensing means for creating a sensed component value representative of the light received from the object, and a current sensing means for determining an amount of electric current used to illuminate th object, wherein the improvement comprises:

a processor connected to said sensing means and said current sensing means, said processor generating a difference value which is a difference between the sensed component value and a product of a stored component value and an intensity correction factor, said processor further producing an error output if said difference value is outside pre-determined limits, said intensity correction factor being a function of a stored current value and a sensed current value.

22. Apparatus for comparing the color of an object to a stored color signature, comprising:

Means for illuminating the object;

Means for providing a plurality of sensed light component values representative of light received from the object;

Means for measuring electric current flowing to said illuminating means;

Means for storing a plurality of stored light component values;

Means for performing a comparison of said plurality of stored light component values to said plurality of sensed light component values; and Means for modifying said comparison in response to a magnitude of said electric current.

* * * * *

UNITED STATES PATENT AND TRADEMARK OFFICE
CERTIFICATE OF CORRECTION

PATENT NO. : 5,042,948

DATED : August 27, 1991

INVENTOR(S) : THOMAS A. FLETCHER

It is certified that error appears in the above-identified patent and that said Letters Patent is hereby corrected as shown below:

Column 4, Line 52, delete "sued" and insert --used--.

Signed and Sealed this

Ninth Day of February, 1993

Attest:

STEPHEN G. KUNIN

Attesting Officer     Acting Commissioner of Patents and Trademarks